United States Patent [19]
Jansen et al.

[11] Patent Number: 6,152,912
[45] Date of Patent: *Nov. 28, 2000

[54] OPTIMIZED HIGH PERFORMANCE SPIRAL-WOUND VASCULAR CATHETER

[75] Inventors: Lex P. Jansen, Pleasanton; Peter Kyone Park, Santa Clara; Gene Samson; Henry Nita, both of Milpitas; Erik T. Engelson, Menlo Park, all of Calif.

[73] Assignee: Target Therapeutics, Inc., Fremont, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/872,215

[22] Filed: Jun. 10, 1997

[51] Int. Cl.[7] .................................................. A61M 25/00
[52] U.S. Cl. ........................... 604/526; 604/523; 604/524; 604/527
[58] Field of Search ..................................... 604/202, 200, 604/264, 96, 95, 523–33

[56] References Cited

U.S. PATENT DOCUMENTS

| | | |
|---|---|---|
| 0,243,396 | 6/1881 | Pfarre . |
| 2,211,975 | 8/1940 | Hendrickson . |
| 2,437,542 | 3/1948 | Krippendorf . |
| 3,174,851 | 3/1965 | Buehler et al. . |
| 3,351,463 | 11/1967 | Rozner et al. . |
| 3,416,531 | 12/1968 | Edwards . |
| 3,753,700 | 8/1973 | Harrison et al. . |
| 3,757,768 | 9/1973 | Kline . |
| 3,924,632 | 12/1975 | Cook . |
| 4,425,919 | 1/1984 | Alston, Jr. et al. . |
| 4,430,083 | 2/1984 | Ganz et al. . |
| 4,484,586 | 11/1984 | McMickle et al. . |
| 4,516,972 | 5/1985 | Samson . |
| 4,657,024 | 4/1987 | Coneys . |

(List continued on next page.)

FOREIGN PATENT DOCUMENTS

| | | |
|---|---|---|
| 0098100 | 1/1984 | European Pat. Off. . |
| 0421650 | 4/1991 | European Pat. Off. . |
| 0661072 | 7/1995 | European Pat. Off. . |
| 2613231 | 10/1988 | France . |
| 3642107 | 6/1987 | Germany . |
| 2-283346 | 11/1990 | Japan . |
| 3-023830 | 1/1991 | Japan . |
| 5-56910 | 3/1993 | Japan . |
| 5-220225 | 8/1993 | Japan . |
| WO 92/07507 | 5/1992 | WIPO . |
| WO 93/05842 | 4/1993 | WIPO . |
| WO 93/15785 | 8/1993 | WIPO . |

*Primary Examiner*—Glenn K. Dawson
*Assistant Examiner*—Patricia Bianco
*Attorney, Agent, or Firm*—Morrison & Foerster LLP

[57] ABSTRACT

This is a catheter suitable for accessing a tissue target within the body, typically a target which is accessible through the vascular system. Central to the concept of the catheter is the use of a reinforcing member wound within the catheter body in such a way to create a catheter having an exceptionally thin wall, excellent kink-resistance, and controlled stiffness. The catheter assembly desirably is constructed of: (a) an inner, polymeric, lubricious liner, (b) a first, helically wound coil over at least the more distal portions of the inner liner, (c) a second, helically wound coil exterior to the first coil located at least on the more proximal portion of the assembly, and (d) one or more outer polymeric coverings exterior to the second coil. Further polymeric layers may also be placed between the outer polymeric covering and the helically wound coils. The outer polymeric covering may be composed of a series of different polymeric compositions to provide suitably differing flexibilities to the assembly. The catheter assembly is quite easy to produce. The helically wound coils are desirably bound to the assembly via the use of radio-opaque bands or coils and preferably are continuously wound from a single member. The distal-most portion of the catheter assembly is very flexible but highly kink resistant.

15 Claims, 5 Drawing Sheets

U.S. PATENT DOCUMENTS

| | | |
|---|---|---|
| 4,676,229 | 6/1987 | Krasnicki et al. . |
| 4,682,607 | 7/1987 | Vaillancourt et al. . |
| 4,721,117 | 1/1988 | Mar et al. . |
| 4,737,153 | 4/1988 | Shimamura et al. . |
| 4,739,768 | 4/1988 | Engelson . |
| 4,806,182 | 2/1989 | Rydell et al. . |
| 4,817,613 | 4/1989 | Jaraczewski et al. . |
| 4,832,681 | 5/1989 | Lenck . |
| 4,899,787 | 2/1990 | Ouchi et al. . |
| 4,981,478 | 1/1991 | Evard et al. . |
| 4,985,022 | 1/1991 | Fearnot et al. . |
| 5,019,057 | 5/1991 | Truckai . |
| 5,037,404 | 8/1991 | Gold et al. . |
| 5,057,092 | 10/1991 | Webster, Jr. . |
| 5,069,674 | 12/1991 | Fearnot et al. . |
| 5,176,660 | 1/1993 | Truckai . |
| 5,178,158 | 1/1993 | de Toledo . |
| 5,180,376 | 1/1993 | Fischell . |
| 5,184,627 | 2/1993 | de Toledo . |
| 5,217,482 | 6/1993 | Keith . |
| 5,222,949 | 6/1993 | Kaldany . |
| 5,248,305 | 9/1993 | Zdrahala . |
| 5,254,107 | 10/1993 | Soltesz . |
| 5,295,978 | 3/1994 | Fan et al. . |
| 5,313,967 | 5/1994 | Lieber et al. . |
| 5,334,166 | 8/1994 | Palestrant . |
| 5,397,306 | 3/1995 | Nobuyoshi et al. . |
| 5,443,907 | 8/1995 | Slaikeu et al. . |
| 5,454,795 | 10/1995 | Samson . |
| 5,554,139 | 9/1996 | Okajima . |
| 5,702,373 | 12/1997 | Samson ................................ 604/202 |
| 5,951,539 | 9/1999 | Nita et al. ............................. 604/526 |

OPTIMIZED HIGH PERFORMANCE SPIRAL-WOUND VASCULAR CATHETER

FIELD OF THE INVENTION

This invention is a surgical device. In particular, it is a catheter suitable for accessing a tissue target within the body, typically a target which is accessible through the vascular system. Central to the invention is the use of a reinforcing member wound within the catheter body in such a way to create a catheter having an exceptionally thin wall, excellent kink-resistance, and controlled stiffness. The catheter assembly desirably is constructed of: (a) an inner, polymeric, lubricious liner, (b) a first, helically wound coil over at least the more distal portions of the inner liner, (c) a second, helically wound coil exterior to the first coil located at least on the more proximal portion of the assembly, and (d) one or more outer polymeric coverings exterior to the second coil. Further polymeric layers may also be placed between the outer polymeric covering and the helically wound coils. The outer polymeric covering may be composed of a series of different polymeric compositions to provide suitably differing flexibilities to the assembly. The catheter assembly is quite easy to produce. The helically wound coils are desirably bound to the assembly via the use of radio-opaque bands or coils and preferably are continuously wound from a single member. The distal-most portion of the catheter assembly is very flexible but highly kink resistant.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. Size, kink-resistance, trackability (the ability to follow a guidewire into and through tortuous vasculature), and flexibility are the physical parameters principally contributing to the utility of the class of catheters.

One such treatment of circulatory system diseases is via angioplasty (PCTA). Such a procedure uses catheters having balloons on their distal tips. It is similarly common that those catheters are used to deliver a radiopaque agent to the site in question prior to the PCTA procedure to view the problem prior to treatment.

Often the target to be accessed by catheter is within a soft tissue such as the liver or the brain. These are difficult sites to reach. The catheter is usually introduced through a large artery such as those found in the groin or in the neck and then must be passed through ever-narrower regions of the arterial system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above. Yet at the same time the catheters must not cause significant trauma to the blood vessel or to the surrounding tissue during their passage. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have supple distal ends which are carried by blood flow to the target site.

The invention combines one or more polymeric tubes with one or more spirally wound ribbons to control the stiffness of the resultant catheter section or body. The construction technique allows the production of catheters having very small diameters but which are very flexible and kink resistant.

The use of ribbons or wires in winding a catheter body is not a novel concept. Typical background patents are discussed below.

Multi-Wrap Catheters

There are a number of catheters discussed in the literature which utilize catheter bodies having multiply wrapped reinforcing material. These catheters include structures having braided bands or ones in which the spirally wound material is simply wound in one direction and the following layer or layers are wound in the other.

Krippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer. There is no indication that this device is of the flexibility described herein. Additionally, it appears to be the type which is used in a region other than in the body's periphery or in its soft tissues.

Similarly, U.S. Pat. No. 3,416,531, to Edwards, shows a catheter having "braiding-edge" walls. The device further has additional layers of other polymers such as TEFLON and the like. The strands found in the braiding in the walls appear to be threads having circular cross-sections. There is no suggestion of constructing a device using ribbon materials. Furthermore, the device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiralled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multilayered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is an aramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire. It would not meet the flexibility criteria required of the inventive catheter described herein.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Patent No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and the filaments are wound at a tension of about 250,000 lb./in.$^2$ (of cross-section) or more. The flat strands themselves are said to have a width of between 0.006 and 0.020 inches and a thickness of 0.0015 and 0.004 inches. There is no suggestion to use these concepts in devices having the flexibility and other configurations described below.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

Single-Layer, Reinforced Catheters

There are a variety of catheters which, unlike the devices discussed above, utilize but a single layer of reinforcing material.

For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975, to Hendrickson, shows a similar device also comprising a stainless steel wire 15 embedded in the inner wall of a rubber catheter.

U.S. Pat. No. 3,757,768, to de Toledo, shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth". There is no suggestion to separate the windings of the coil in any fashion.

U.S. Pat. No. 4,430,083 describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides the heat-shrunk tubing with footing for a tight fit.

U.S. Pat. No. 4,567,024, to Coneys, shows a catheter which employs a set of helical strips within the wall of the catheter. However, the helical strips are of a radiopaque material, e.g., fluorinated ethylene-propylene. It is not clear that the blended radiopaque material necessarily provides any physical benefit other than the ability to allow the catheter shaft to be seen when viewed with a fluoroscope.

U.S. Pat. No. 4,737,153, to Shimamura et al., describes a device which is characterized as a "reinforced therapeutic tube" and which uses a spiral reinforcing material embedded within the wall of the device.

U.S. Pat. No. 5,069,674, to Feamot et al. (and its parent, U.S. Pat. No. 4,985,022), shows a small diameter epidural catheter having a distal tip made up of a stainless steel wire which is helically wound and placed within a tubular sheath or tube. There is no suggestion within the patent that the interior coil be made to adhere to the outer tubular sheath.

Similarly, U.S. Pat. No. 5,178,158, to de Toledo, shows what is characterized as a "convertible wire for use as a guidewire or catheter". The patent describes a structure which comprises an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath (40) of Teflon that extends from the proximal end (12) to the distal end (14) of the device. The overlying sheath (40) may extend or overhang at the proximal or the distal end of the catheter. The distal tip portion (13) is said to be "flexible, soft, and floppy". The PCT Published Application corresponding to this patent is WO 92/07507.

U.S. Pat. No. 5,184,627 shows a guidewire suitable for infusion of medicaments to various sites along the guidewire. The guidewire is made up of a helically wound coil having a polyimide sheath enclosing its proximal portion and a Teflon sheath tightly covering the entire wire coil.

U.S. Pat. No. 5,313,967, to Lieber et al., shows a medical device a portion of which is a helical coil which, apparently, may include an outer plastic sheath in some variations. Apparently, a secondary helix of a somewhat similar design, in that it is formed by rotating a flat wire or the like along its longitudinal axis to form a screw-like configuration, is included within the helical coil to provide axial pushability and torque transmission.

The PCT application, WO 93/15785, to Sutton et al., describes kink-resistant tubing made up of a thin layer of an encapsulating material and a reinforcing coil. As is shown in the drawings, the supporting material is embedded within the wall of the tubing in each instance.

The PCT application bearing the number WO 93/05842, to Shin et al., shows a ribbon-wrapped catheter. The device is shown as a section of a dilatation catheter. The inner section 34 is a helically wound coil and is preferably a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon to enhance lubricity or provide other advantages. In some embodiments, the spring coil has been plated with gold." The document does not suggest that the coil be made to adhere to the outer polymeric jacket using an adhesive.

Endoscope Structures

Various endoscopic structures, used primarily in sizes which are larger than endovascular catheters utilize structures including stiffener materials.

U.S. Pat. No. 4,676,229, to Krasnicki et al., describes an endoscopic structure 30 having an ultrathin walled tubular substrate 31 formed of a lubricious material such as TEFLON. The structure contains a filament supported substrate. The filament is coated with and embedded into a filler material, typically an elastomeric material. A highly lubricious outer coating 35, all as shown in FIG. 2, forms the outer layer of the device. FIG. 3 in Krasnicki et al., describes another variation of the endoscopic device in which a different selection of polymer tubing is utilized but the placement of the filamentary support remains varied in an intermediate material of an elastomer. In some variations of the device, the filament is strongly bonded to the inner tubular substrate using an adhesive 37 "such as an epoxy cement having sufficient bond strength to hold the filament to the substrate as it is deformed into a tight radius." See, column 3, lines 50 and following.

U.S. Pat. No. 4,899,787, to Ouchi et al. (and its foreign relative, German Offenlegungshrifft DE-3242449) describes a flexible tube for use in an endoscope having a flexible, basic tubular core structure made up of three parts. The three parts are an outer meshwork tube, an intermediate thermoplastic resin tube bonded to the outer meshwork tube, and an inner ribbon made of a stainless steel or the like which is adherent to the two polymeric and meshwork tubes such that the resin tube maintains an adherent compressive pressure in the finished flexible tube. The patent also suggests the production of an endoscope tube having "flexibility which varies in step-wise manner from one end of the tube to the other . . . [and is produced] by integrally bonding two or more thermoplastic resin tube sections formed of respective resin materials having different hardnesses to the outer surface of the tubular core structure . . . ". See, column 2, lines 48 and following.

U.S. Pat. No. 5,180,376 describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counter-wound metal ribbons is also described. No suggestion of the use of an adhesive is made in the patent.

European Patent Application 0,098,100 describes a flexible tube for an endoscope which uses a helically wound metallic strip having a braided covering contiguous to the outer surface of the coil and having still further out a polymeric coating 9. Interior to the coil is a pair of slender flexible sheaths which are secured to a "front-end piece 10" by soldering.

Japanese Kokai 2-283,346, describes a flexible endoscope tube. The tubular outer shell is made up of two layers of a high molecular weight laminated material. The tube also has an inner layer of an elastic material and interior to it all is a metallic ribbon providing stiffening.

Japanese Kokai 03-023830, also shows the skin for flexible tube used in an endoscope which is made up of a braid 3 prepared by knitting a fine wire of a metal with a flexible portion 2 which is prepared by spirally winding an elastic belt sheet-like material and a skin 4 with which the whole outer surface of the device is covered. The document appears to emphasize the use of a particular polyester elastomer.

Japanese Kokai 5-56,910, appears to show a multi-layered endoscope tube made up of layers of the spiral wound metallic ribbon covered by a polymeric sheath.

French Patent Document 2,613,231, describes a medical probe used with an endoscope or for some other device used to stimulate the heart. The device appears to be a helix having a spacing between 0 and 0.25 mm (See page 4, line 20) preferably rectangular in cross section (See Page 4, Line 1) and of a multi-phase alloy such as M35N, SYNTACOBEN, or ELGELOY (See Page 4).

German Offenlegungshrifft DE-3642107 describes an endoscope tube, formed of a spiral tube, a braid formed of fibers interwoven into a net (which braid is fitted on the outer peripheral surface of the spiral tube), and a sheath covering the outer peripheral surface of the braid.

None of the noted devices have the structure required by the claims recited herein.

Other Anti-kinking Configurations

U.S. Pat. No. 5,222,949, to Kaldany, describes a tube in which a umber of circumferential bands are placed at regular intervals along a catheter shaft. The bands may be integrated into the wall of the catheter. A variety of methods for producing the bands in the tubular wall are discussed. These methods include periodically irradiating the wall to produce bands of a higher degree of cross-linking.

European Patent Application No. 0,421,650-A1 describes a method for producing a catheter from a roll of polymer film while incorporating other materials such as tinfoil elements or the like.

None of the documents cited above provides a structure required by the disclosure and claims recited below, particularly when the flexibility and ability to resist kinks is factored into the physical description of the devices.

SUMMARY OF THE INVENTION

This invention is a catheter section made up of one or more spirally wound reinforcement ribbons or wires placed between an outer polymeric covering and in inner polymeric liner.

The preferred stiffener ribbon is, in its most basic form, a single strand of ribbon wound first in a single direction and preferably further wound back over at least a proximal portion of the catheter to form a region of double thickness. The ribbons are may be metallic and most desirably are of a super-elastic alloy or stainless steel, but may be of other materials. The helically wound coils may be in contact either with the outer polymeric covering or the inner polymeric liner. Most preferably the distal-most end of each of the helical windings is held to the inner polymeric liner by a radio-opaque band or coil. The inner polymeric liner is preferably of a lubricious material which may be extruded or cast in thin sections.

Wise choices of materials permit this inventive catheter to be of a smaller overall diameter with a superior kink diameter. One variation of this invention involves telescoping catheters with an inner catheter of this construction, perhaps with an inner guidewire. The catheter may be wholly constructed of materials which are stable to radioactive sterilization procedures.

DESCRIPTION OF THE INVENTION

This invention is a thin-walled, highly flexible, kink-resistant catheter assembly. It is a composite device having multiple sections with different or varying stiffnesses. It has an inner-most layer, preferably polymeric, and most preferably of a lubricious polymer such as polytetrafluoroethylene. The inner layer preferably extends from the proximal e.and of the catheter assembly to the distal end. The continuity of the inner layer is a matter of manufacturing convenience and efficiency. The design includes a helically wound ribbon stiffener coaxial with and typically is contiguous to both the polymeric outer layer and the inner liner although additional layers of polymeric material may be placed variously between the coils and the polymeric outer layer and the inner liner if so desired. The inner liner forms the inner lumen of the catheter. The outer polymeric covering typically is constructed from a number of sections of polymers having different flexural moduli placed axially nose-to-tail. The helical coils are preferably attached to the inner layer by radio-opaque bands or coils. Those coils are desirably formed of a single, continuous, super-elastic alloy or stainless steel member (e.g., a ribbon or wire) wound from the distal end to the proximal end and then back typically to a point near (or, perhaps, at) the distal end of the catheter assembly. The pitch of the wound coils may be varied as desired. Additional layers of wound coil may be applied as necessary or desirable to attain appropriate physical characteristics. The catheter is configured so that at least the distal portion of the catheter has a critical bend diameter of no more than 3.0 mm, preferably no more than 2.5 mm, more preferably no more than 1.5 mm, and most preferably no more than 1.0 mm.

Figure 1:
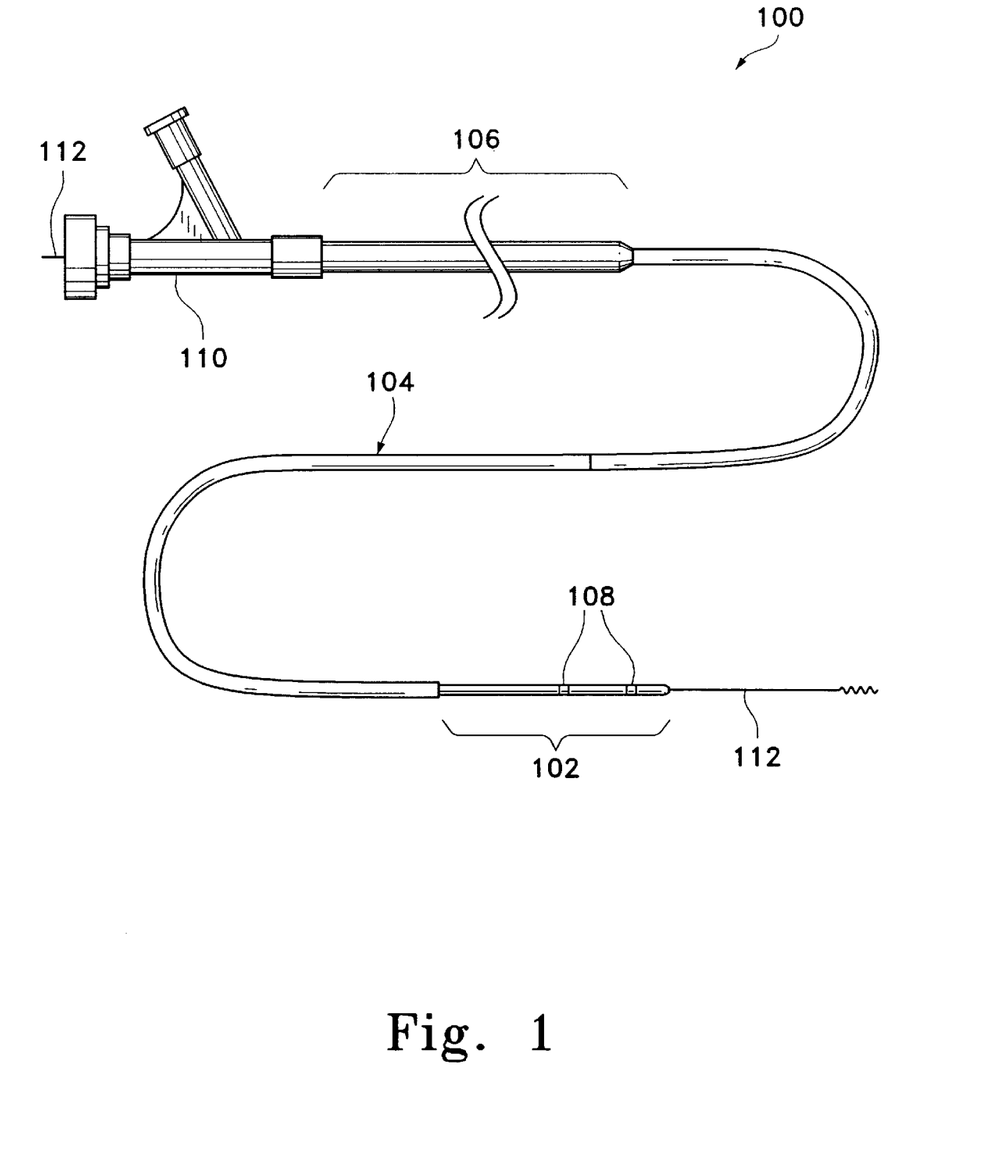
FIG. 1 shows, in side view, a typical three section catheter.

A typical multi-section catheter (100) which may incorporate the concepts of this invention is shown in FIG. 1. Such a catheter is described in more detail in U.S. Pat. No. 4,739,768, to Engelson, (the entirety of which is incorporated by reference) and is particularly suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever more smaller vascular areas. This smaller diameter requires a concomitant thinning of the wall section. The thinner section walls may kink or ripple when actively pushed along the guidewire or when vasoocclusive devices are pushed through the catheter's lumen. The typical configuration shown in FIG. 1 has a distal section (102) having significant flexibility, an intermediate section (104) which is typically less flexible, and a long proximal section (106) which in turn is least flexible. The distal section (102) is flexible and soft to allow deep penetration of the extraordinary convolutions of the neurological vasculature without trauma. Various known and often necessary accessories to the catheter assembly, e.g., one or more radiopaque bands (108) at the distal region to allow viewing of the position of the distal region under fluoroscopy and a luer assembly (110) for guidewire (112) and fluids access, are also shown in FIG. 1.

The typical dimensions of this catheter are:

| | |
|---|---|
| Overall length: | 60–200 cm |
| Proximal Section (106): | 60–150 cm |
| Intermediate Section (104): | 20–50 cm |
| Distal Section (102): | 2.5–30 cm |

Obviously, these dimensions are only guidelines, are not critical to this invention, and are selected as a function of the malady treated and its site within the body. However, as will be discussed below, use of the spiral wound member permits the walls of the catheter to be somewhat thinner with no diminution of performance, e.g., crush strength or flexibility, and, indeed, usually provides an improvement in performance, particularly in the area of kink-resistance.

FIGS. 2A–2F show a procedure for assembling the catheter shaft making up the catheter assembly of this insertion.

Figure 2A:
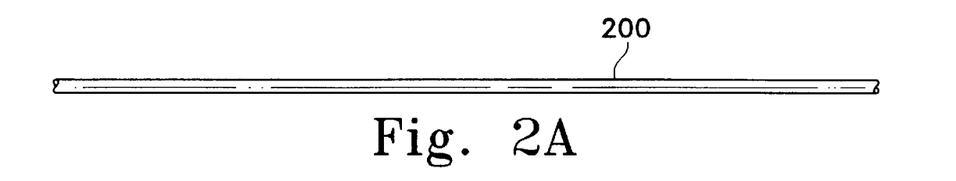
FIGS. 2A–2F schematically depict a method for producing a referred variation of the inventive catheter.

FIG. 2A shows a simple mandrel (200) used as the support for producing the final catheter assembly. The mandrel (200) may be highly malleable, e.g., of copper or silver of the like, for ease of removal (by axial stretching of the mandrel) when the catheter shaft is completely assembled. Or, the mandrel (200) may be of a comparatively non-malleable material such as stainless steel if the mandrel (200) will slide easily from the catheter shaft at the end of the assembly procedure.

Figure 2B:
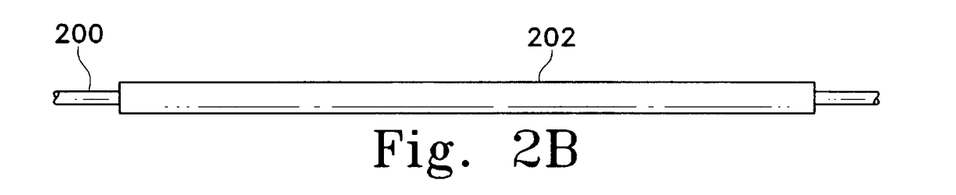

FIG. 2B shows the mandrel (200) with a polymeric tubing (200) placed thereon. This tubing is shown to be a single, continuous component in FIG. 2B and such is preferred, but the polymeric tubing (202) need not be continuous. Shorter sections may make up this portion where, e.g., different stiffness or parameters of slipperiness are needed.

Tubing member (202), which is also referred to as the "inner liner" elsewhere herein, is preferably formed of a lubricious polymer. Suitable polymers include many of the fluorocarbons sold as Teflon although polytetrafluoroethylene is preferred. It is commercially available in thin-wall variations having a wall thickness of 0.5 mils or less. Other suitable lubricious polymers include polypropylene, the Nylons, FEP, polypropylene, and the like.

It is sometimes desirable when using fluorocarbon polymers as the constituent of the "inner liner" (202), that the exterior of the tubing be etched prior to further assembly to provide a suitable bond with any additional outer polymeric coverings. Such etchants are commercially available.

Figure 2C:
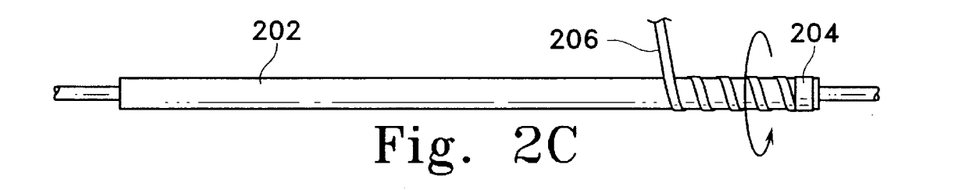

FIG. 2C shows a step in the production of the catheter body in which a radio-opaque band or coil (204) is placed over the ribbon (206) to hold that ribbon (206) in place and the whole subassembly is rotated to wind the ribbon (206) onto the inner tubing member or liner (202).

Although not necessary, it is within the scope of this invention to include an adhesive between the inner polymeric liner (202) and the ribbon (206). Thermoplastic elastomers (such as Hytrel) and ethyl vinyl acetate (EVA) are choices for such an adhesive.

Figure 2D:
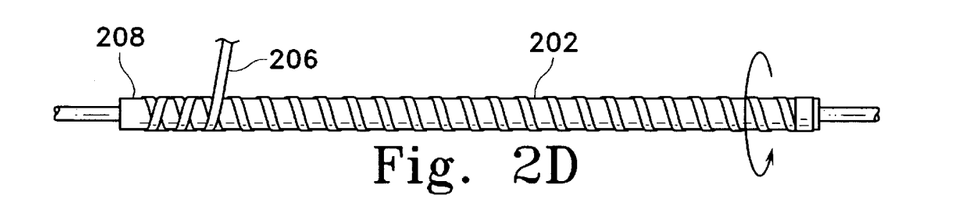

FIG. 2D shows the winding of the ribbon (206) after it has passed to the proximal end (208) of the inner polymeric liner (202) and is being wound back towards the distal end of the subassembly. It should be noted that the pitch of the windings both as the ribbon is passed proximally and as it is returned distally may vary to provide optimum flexibility and kink-resistance.

For instance, the pitch may be narrowed or shortened to provide additional torqueability in the proximal end of the assembly. One embodiment is shown in FIG. 2G, where a pitch of ribbon (206) is narrowest at proximal end (106) to provide the additional torqueability. Similarly, in the distal end of the catheter where torqueability is less a concern and kink resistance and flexibility are, the spacing between turns may be increased to optimize those physical parameters. Likewise in FIG. 2G, ribbon (206) has a pitch is widest at distal end (102).

The spiral wound ribbon (206) shown in FIGS. 2A–2F may be of a variety of different materials. Although metallic ribbons are preferred because of their strength-to-weight ratios, fibrous materials (both synthetic and natural) may also be used. Desirable, because of cost, strength, and ready availability are stainless steels (SS308, SS304, SS318, etc.) and tungsten alloys. The Young's modulus of a stainless steel such as 304SS is perhaps three times that of a super-elastic alloy. consequently, a ribbon using such a stainless steel may be much smaller with comparable strength. In certain applications, particularly smaller diameter catheter sections, more malleable metals and alloys, e.g., gold, platinum, palladium, rhodium, etc. may be used. A platinum alloy with a few percent of tungsten is preferred partially because of its radiopacity.

The class of alloys known as super-elastic alloys is also a desirable selection. Preferred super-elastic alloys include the class of titanium/nickel materials known as nitinol—alloys discovered by the U.S. Navy Ordnance Laboratory. These materials are discussed at length in U.S. Pat. No. Nos. 3,174,851 to Buehler et al., U.S. Pat. No. 3,351,463 to Rozner et al., and U.S. Pat. No. 3,753,700 to Harrison et al. These alloys are commercially available in the small ribbons required by the invention described here, but for very high performance catheters are excellent choices. Other super-elastic or high performance alloys suitable for this use include M35N, SYNTACOBEN, or ELGELOY and the like.

Metallic ribbons (206) that are suitable for use in this invention are desirably between 0.25 mil and 1.5 mil (preferably 0.25–0.50 mils) in thickness and 1.0 mil and 8.0 mil (preferably less than 3.0 mils, and most preferably 1.0–3.0 mils) in width, particularly when stainless steels are used. By the term "ribbon", we intend to include elongated shapes, the cross-section of which are not square or round and may typically be rectangular, oval or semi-oval. They should have an aspect ratio of at least 0.5 (thickness/width). In any event, for stainless steels, the thickness and width may be somewhat finer, e.g., down to 0.25 mil and 1.0 mil, respectively.

Suitable non-metallic ribbons include high performance materials such as those made of polyaramids (e.g., KEVLAR), liquid crystal polymers (LCP's), and carbon fibers.

Figure 2E:
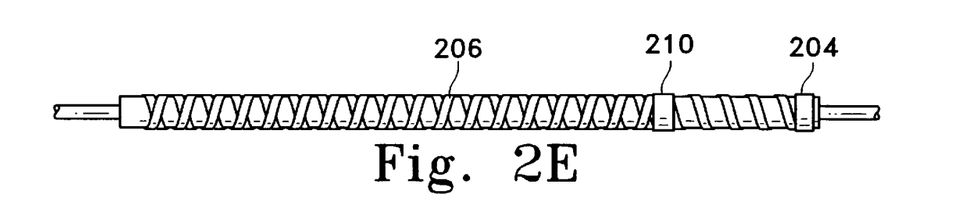

FIG. 2E shows the completed wrapping or winding of the helically wound coil (296) and its final attachment to the subassembly via a radio-opaque member (206). Radio-opaque members (204, 210) are generally solid bands, bands with axial cuts, or coils of a malleable radio-opaque metal as discussed above. This variation is the one we call the "continuous wind" variation since ribbon (206) is a continuous band.

As was the case above, it is within the scope of this invention to place an adhesive on the exterior of the assembly at this point to assist in providing adherence of the ribbon (206) and inner liner (202) to the outer polymeric coverings (212, 214, 216, and 218) discussed below. The use of adhesives in this step or in that mentioned above are completely depend principally upon the choice of materials in those outer polymeric coverings.

Figure 2F:
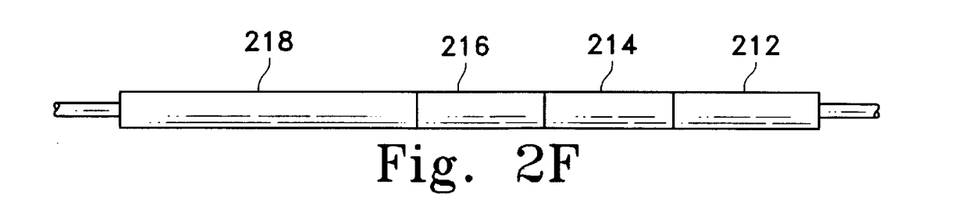
Figure 2G:
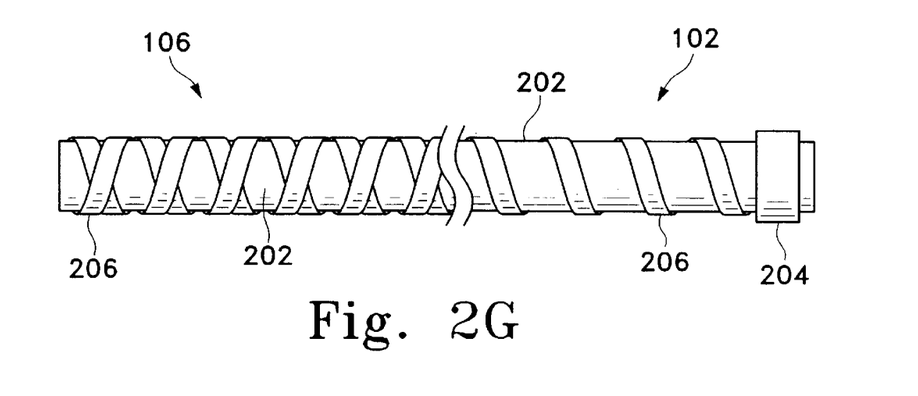
FIG. 2G shows a variation of the invention in which a ribbon has a wider pitch on a distal end of the inventive catheter and a narrower pitch on a proximal end of the inventive catheter.

FIG. 2F shows the assembly with a number of outer polymeric tubing sections (212, 214, 216, 218) as placed on the exterior with the ribbon (206). The distal-most section (212) is typically the softest and most flexible. As may be apparent from a comparison of FIGS. 2E and 2F, section (212) is typically placed only over the distal portion of the assembly in which the ribbon (206) is wound in a single layer. Desirably, the proximal radio-opaque marker (210) and the distal radio-opaque marker (204) fluoroscopically bracket the distal section of the assembly.

Sections (214, 216, and 218) are axially contiguous tubing markers and are generally harder and less flexible, e.g., as measured by durometer and flexual modules, as the proximal end is approached. We have found that three sections of increasing flexibility is generally optimum and consequently sections (214, 216) of the outer polymeric covering may be combined.

A wide variety of polymers are acceptable as materials for the outer polymeric covering sections (212, 214, 216, 218). Shrink wrap polyethlene, e.g., polyethlene tubing containing a sufficient amount of a crosslinking agent such as EVA, which has been stretched and irradiated, is suitable. We prefer various blends such as CARBOTHANE, PEBAX, TECOFLEX, and TECOTHANE, often containing polyurethane. Although these materials are not shrinkwrapple polymers per se, they may be accurately placed on the catheter shaft assembly in the following manner. The various sections of polyurethane tubing are cut to length and placed over the wrapped catheter shaft subassembly shown in FIG. 2E. A shrink wrappable layer of polyethlene tubing is then placed over the polyurethane tubing and heated so to shrinkwrap the polyethelene and pull the polyurethane into intimate contact with the reinforcing member (206) winding and perhaps with the inner liner (202). Some thought must be had for selection of polyurethane composition having appropriate $T_g$'s with relation to the shrink-wrap temperature of the polyethlene layer. The polyethylene layer may be left in place or, desirably, be stripped away exposing the polyurethane. Polymers suitable for this service include known materials such as polyethylene, polyvinylchloride (PVC), ethylvinylacetate (EVA), polyethylene terephalate (PET), and their mixtures and copolymers. One very useful class of polymers are the thermoplastic elastomers, particularly polyesters. Typical of this class is HYTREL. This is not to exclude the use of other polymers, depending on the section of the catheter. For instance, the tubing may be of any of a variety of polymers, variously stiff or flexible. For instance, for section (218), the polymer may be a polyimide, polyamides such as the Nylons, high density polyethylene (HDPE), polypropylene, polyvinylchloride, various fluoropolymers (for instance: PTFE, FEP, vinylidene fluoride, their mixtures, alloys, copolymers, block copolymers, etc.), polysulfones or the like. Blends, alloys, mixtures, copolymers, block copolymers, of these materials are also suitable, if desired.

If a more flexible section is required, the outer tubing member may be a polyurethane, low density polyethylene (LDPE), polyvinylchloride, THV, etc. and other polymers of suitable softness or modulus of elasticity. The wall thickness of the outer tubing member (206) may be as thin as 0.5 mil and as thick as 10 mil, depending upon catheter usage, portion of the catheter, polymer choice, and the style of catheter.

Typically, the wall thickness of the inner liner (202) will be between 0.5 and 3.0 mils. This dimension is obviously only a range and each catheter variation must be carefully designed for the specific purpose to which it is placed.

It should also be noted at this point that each of the polymers discussed herein may be used in conjunction with radiopaque material such as barium sulfate, bismuth trioxide, bismuth carbonate, powdered tungsten, powdered tantalum, or the like so that the location of the various pieces of tubing may be radiographically visualized within the vessel.

At this point, the mandrel (200) may be removed and assembly of the catheter shaft is complete. Of course, as shown below, the addition of a proximal fluid handling member, e.g., with a Luerlock, is necessary and subsequent treatment with a material to provide enhanced lubricity perhaps by bonding with a hydrophilic polymer coating, is desirable.

Figure 3:
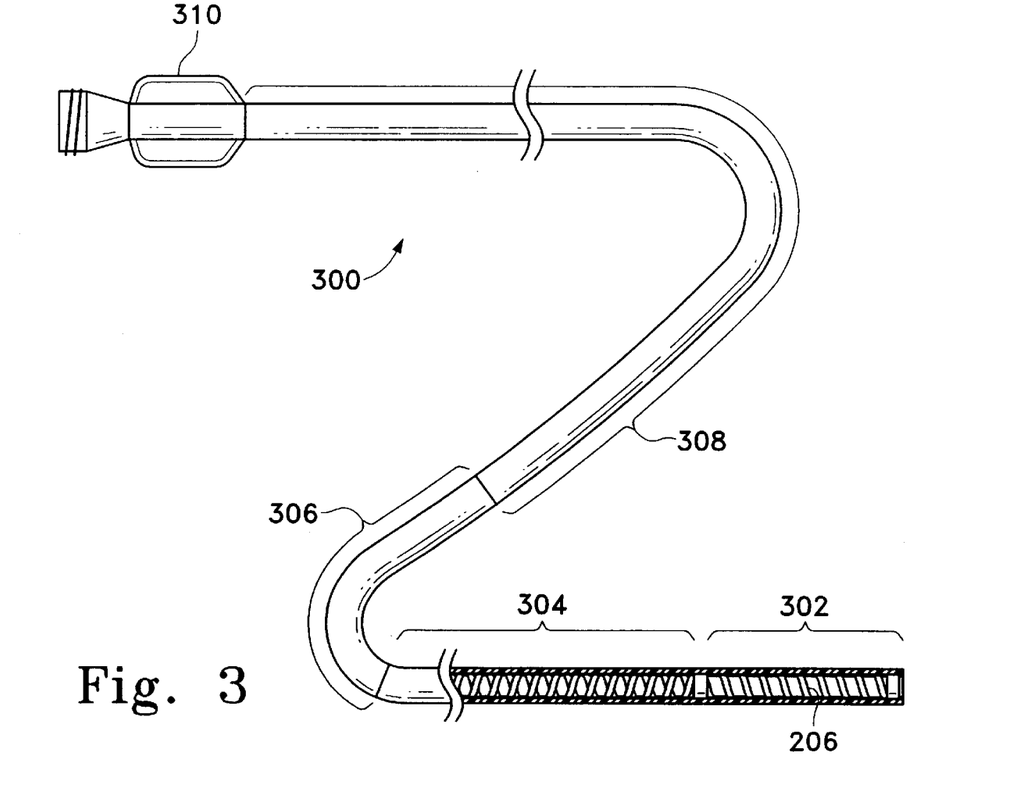
FIG. 3 shows, in partial and cross-section, a variation of the invention made using the procedure of FIGS. 2A–2F.

FIG. 3 shows the variation of the inventive catheter (300) as finally assembled using the procedure shown in FIGS. 2A–2E. The numerous sections (302, 304, 306, and 308) of increasing stiffness proximally may also be seen. The connector portion (310), located proximally, allowing connection with fluid delivery means or guideline handling devices.

The single layer of ribbon (206) is shown in the cutaway of distal-most section (302). The multiple layers of ribbon are shown in the cutaway of the next more proximal section (304).

Figure 4:
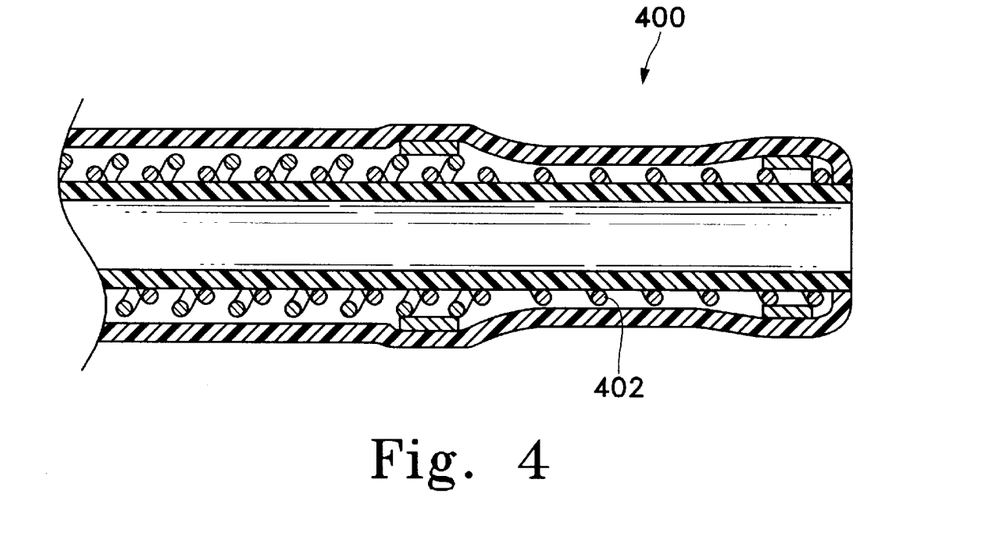
FIGS. 4 and 5 show, in cross-section, a distal tip of the inventive catheter.

FIG. 4 shows a cross-section of the distal end (400) of the variation shown in FIG. 3 but with the exception that the helical coil (402) is formed of a wire rather than a ribbon. By "wire" we mean a member having a round, square, oval, or similar cross-section with an aspect ratio of 0.5 (thickness/width) or less.

Figure 5:
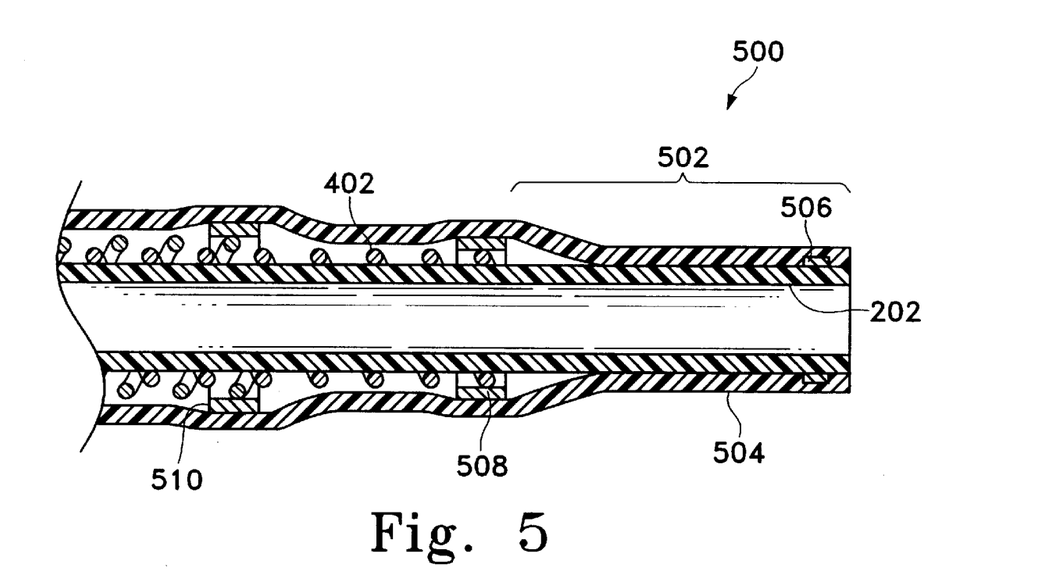

FIG. 5 shows a cross-section of the distal end (500) of a variation in which the helically wound coil (402) does not extend to the distal tip. In this variation, the most distal section (502) is comprised of an outer layer (504) and an inner polymeric liner ((202). Multiple radio-opaque markers (506, 508, 510) are shown. Markers (508, 510) are used to attach the helical coil (402) ends to the inner liner (202) and depict ends of the various flexibility region.

Typical of the catheters made using this invention are in the 1.5 French to 5 French range. The typical inner diameter of such catheters is then 20 mils to 42 mils. However, micro-catheters may be made using these concepts having outside diameters of 18 mils to 34 mils. The inner diameter of those catheters was 11 mils to 20 mils. The invention is not limited to such sizes, however.

As was noted above, the most distal portion of the distal section of this catheter (and preferably other sections as well) have a critical bend diameter of no more than 3.0 mm, preferably no more than 2.5 mm, more preferably no more than 1.5 mm, and most preferably no more than 1.0 mm. To some extent, the critical bend diameter is also dependent upon the diameter of the catheter section and its components. For instance, we have made 3 French catheter section of the type shown in FIG. 2 (of stainless steel ribbon) with critical bend diameters less than 2.5 mm. Similarly, we have made catheter sections such as the inner catheter (275) shown in FIG. 9 with an outer diameter of 0.018" (of platinum-tungsten alloy ribbon) with bend diameters less than 1.0 mm.

Figure 6A:
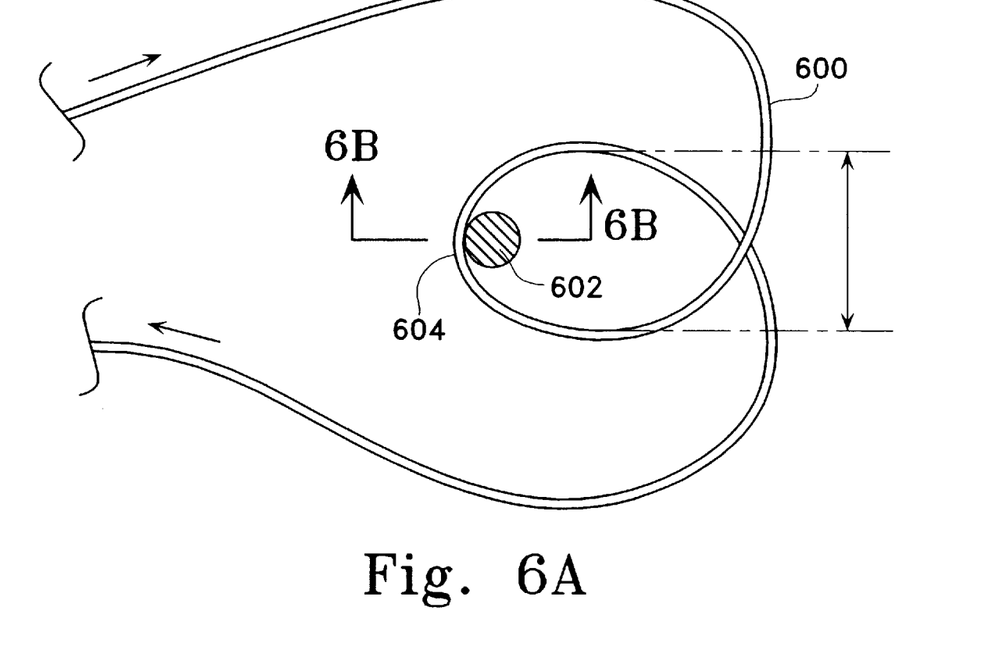
FIGS. 6A and 6B show details of methods for determining the "critical bend diameter" for a catheter.
Figure 6B:
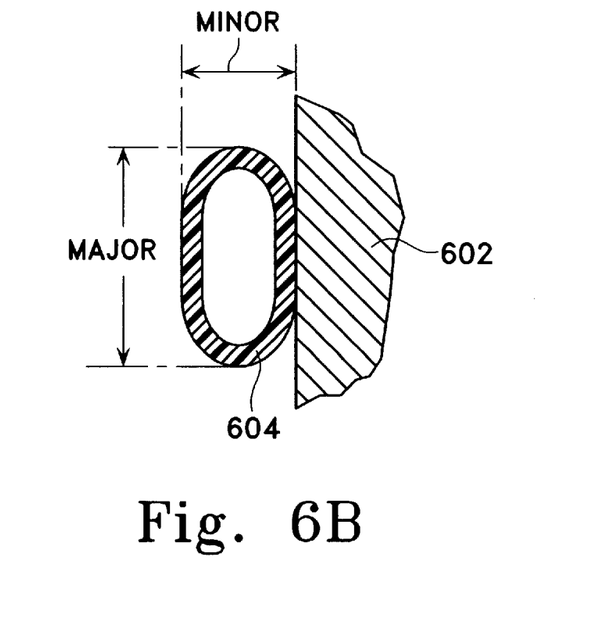

The test we utilize for critical bend diameter determination uses a test shown schematically in FIGS. 6A and 6B.

In general, as shown in FIG. 6A, a catheter section (600) is placed between two plates (desirably of plastic or glass or the like for visibility) and often with an optional peg (602) to hold the catheter section (600) loop in place. The ends of the catheter are then pulled until a kink appears in the body of the catheter. Alternatively, the ratio of the outer diameters (major diameter:minor diameter) as measured at apex (604) reaches a value of 1.5. FIG. 6B shows the cross section of the catheter sector at (604) and further shows the manner in which the major diameter and the minor diameter are measured. These two methods provide comparable results although the latter method is more repeatable.

EXAMPLE

We constructed an intravascular catheter using the concepts of this invention. The device was about 150 cm. overall and had an inner tubing member of TFE. That inner tubing member had a wall thickness of about 0.75 mil. The wall thickness of the inner liner was difficult to determine because the tubing is stretched from its original configuration. A 0.7 mil thickness of a polyurethane blend was then applied to the TFE inner lining. This subassembly (having a mandrel in its center) was then mounted in a lathe-like apparatus to add the helically wound reinforcing member. The reinforcing member was a ribbon of 304 SS having a thickness of 0.75 mil and a width of 3 mils. It was secured to the distal end using a platinum band which was about 1 mil in length. The assembly was rotated in the coil-winder to wind the ribbon from the distal end to the proximal end. At the proximal end, the direction of the ribbon wind was changed so that the ribbon ws being wound towards the distal end. The ribbon was wound to the end of the catheter so that a double layer of ribbon was found from distal end to proximal end. Several sections of polymeric tubing formed of PEBAX (a thermoplastic elastomer sold by Elf Atochem North America), each having a different flexural modulus, were placed on the shaft assembly. A shrink-wrappable polyethylene tubing was then placed on the exterior of the PEBAX tubing and the assembly was heated. The polyethylene shrink-wrap pulled the PEBAX tubing down to the coil surface. The polyethylene shrink-wrap tubing was then stripped from the exterior of the assembly. The distal tip had a kink resistance of about 1.0 mm.

This invention has been described and specific examples of the invention have been portrayed. The use of those specifics is not intended to limit the invention in any way. Additionally, to the extent that there are variations of the invention which are within the spirit of the disclosure and yet are equivalent to the inventions found in the claims, it is our intent that this patent cover those variations as well.

We claim as our invention:

1. A catheter comprising:
    an elongate tubular member having a proximal end and a distal end, comprising:
    a.) tubular polymeric inner liner having a passageway defining an inner lumen and an outer surface,
    b) a stainless steel ribbon reinforcing member having a width and thickness, the ribbon reinforcing member being spirally wound upon the inner liner from the distal end in a proximal direction towards the proximal end forming a first layer,
    c) the ribbon reinforcing member being further wound exterior to the first layer in a distal direction from the proximal end upon a portion of the first layer forming a second layer, the second layer of the ribbon reinforcing member terminating at a point proximal of the distal end, and
    d.) at least one exterior tubing member exterior to the second layer.

2. The catheter of claim 1 wherein the first layer of the ribbon reinforcing member is wound from the distal end.

3. The catheter of claim 1 wherein the first layer of the ribbon reinforcing member is wound from a point proximal to the distal end.

4. The catheter of claim 1 wherein the ribbon reinforcing member has a pitch which varies between the proximal end and the distal end.

5. The catheter of claim 1 wherein the ribbon reinforcing member first layer has a pitch which is widest at the distal end.

6. The catheter of claim 1 wherein the ribbon reinforcing member has a pitch which is narrowest at the proximal end.

7. The catheter of claim 1 wherein the ribbon reinforcing member first layer and second layer are a single continuous ribbon.

8. The catheter of claim 1 wherein the thickness of the stainless steel ribbon reinforcing member is between 0.25 to 0.50 mils.

9. The catheter section of claim 1 where the thickness of the ribbon reinforcing member is between 0.5 mil and 2.5 mil and the width of the ribbon reinforcing member width between 2.5 and 8.0 mil.

10. The catheter of claim 1 wherein the inner liner comprises a lubricious polymer.

11. The catheter of claim 10 wherein the lubricious polymer is polytetrafluoroethylene.

12. The catheter of claim 1 wherein the exterior tubing member comprises a polymer selected from the group consisting of polyurethane, polyethylene, ethylvinylacetate, polyethylene terephthalate, polyvinylchloride, and their mixtures and copolymers.

13. The catheter of claim 1 where exterior covering polymer contains a radio-opacifier.

14. The catheter of claim 1 wherein interior liner polymer contains a radio-opacifier.

15. The catheter of claim 1 further comprising a guidewire placed interior to and in slidable position to the inner lumen.

\* \* \* \* \*